United States Patent
Imai et al.

(10) Patent No.: US 10,663,432 B2
(45) Date of Patent: May 26, 2020

(54) GAS SENSOR AND GAS DETECTION METHOD

(71) Applicant: Tianma Japan, Ltd., Kanagawa (JP)

(72) Inventors: Ayuko Imai, Kanagawa (JP); Ken Sumiyoshi, Kanagawa (JP)

(73) Assignee: TIANMA JAPAN, LTD., Kanagawa (JP)

( * ) Notice: Subject to any disclaimer, the term of this patent is extended or adjusted under 35 U.S.C. 154(b) by 0 days.

(21) Appl. No.: 16/380,404

(22) Filed: Apr. 10, 2019

(65) Prior Publication Data

US 2019/0310229 A1 Oct. 10, 2019

(30) Foreign Application Priority Data

Apr. 10, 2018 (JP) .................. 2018-075284

(51) Int. Cl.
*G01N 29/00* (2006.01)
*G01N 29/036* (2006.01)
*G01N 33/00* (2006.01)
*G01N 29/24* (2006.01)

(52) U.S. Cl.
CPC ....... *G01N 29/036* (2013.01); *G01N 29/2431* (2013.01); *G01N 33/005* (2013.01); *G01N 2291/021* (2013.01); *G01N 2291/02809* (2013.01)

(58) Field of Classification Search
CPC ... G01N 2291/021; G01N 2291/02809; G01N 29/036; G01N 29/222; G01N 29/2431; G01N 29/326; G01N 29/348; G01N 33/005; H01M 8/04313
See application file for complete search history.

(56) References Cited

U.S. PATENT DOCUMENTS

| | | | | |
|---|---|---|---|---|
| 5,345,811 A | * | 9/1994 | Alexandrovich, Sr. | G01N 9/002 73/32 A |
| 5,892,152 A | * | 4/1999 | Darling | G01C 19/5691 73/1.77 |
| 5,912,602 A | * | 6/1999 | Takagi | H03H 9/02834 310/313 D |

(Continued)

OTHER PUBLICATIONS

Buma et al., "A High-Frequence, 2-D Array Element Using Thermoelastic Expansion in PDMS", IEEE Transaction S on Ultrasonics, Ferroelectrics, and Frequency Control, vol. 50, No. 9, Sep. 2003, pp. 1161-1176.

*Primary Examiner* — Francis C Gray
(74) *Attorney, Agent, or Firm* — Young & Thompson (57) ABSTRACT

A gas sensor includes: at least one resonator; a vibrator provided on the at least one resonator; at least one converter that converts sound waves outputted from the at least one resonator to an electric signal; and a detection unit that detects a specific gas on the basis of the electric signal attained by conversion by the at least one converter, wherein the vibrator includes at least either one of: a plurality of vibrating bodies that have respectively differing frequency characteristics during vibration, that vibrate a gas inside the at least one resonator, and that output sound waves by resonance of the at least one resonator; and a heater that heats a gas inside the at least one resonator, and that outputs sound waves by resonance of the at least one resonator.

12 Claims, 6 Drawing Sheets

(56) References Cited

U.S. PATENT DOCUMENTS

| | | | |
|---|---|---|---|
| 7,887,636 B2 * | 2/2011 | Nam | H01L 21/02057 |
| | | | 134/1 |
| 2002/0124632 A1 * | 9/2002 | Reiter | G01N 15/0606 |
| | | | 73/24.03 |
| 2008/0000842 A1 * | 1/2008 | Matsuura | B01D 1/16 |
| | | | 210/748.02 |
| 2008/0225296 A1 * | 9/2008 | Liu | G01J 3/433 |
| | | | 356/437 |
| 2015/0022274 A1 * | 1/2015 | Yamazaki | H03B 5/32 |
| | | | 331/156 |

* cited by examiner

GAS SENSOR AND GAS DETECTION METHOD

CROSS-REFERENCE TO RELATED APPLICATION

This Non-provisional application claims priority under 35 U.S.C. § 119(a) on Patent Application No. 2018-75284 filed in Japan on Apr. 10, 2018, the entire contents of which is hereby incorporated by reference.

BACKGROUND

The present disclosure relates to a gas sensor and a gas detection method.

Hydrogen is widely used in chemical products such as fuel cells, synthetic resins, and pharmaceutical products. Hydrogen gas has a low molecular weight and therefore has a tendency to leak, and additionally has a wide explosive concentration range, and thus, techniques to measure the concentration of hydrogen gas are important. Hydrogen has a low molecular weight and the speed of sound in hydrogen gas is faster than in other gases, and thus, there are techniques for measuring the concentration of hydrogen gas by detecting changes in the speed of sound.

Non-Patent Document 1 (IEEE Transactions on Ultrasonics, Ferroelectrics, and Frequency Control, VOL. 50, No. 9, SEPTEMBER 2003) discloses a technique in which the hydrogen gas concentration is measured by causing a gas inside a container provided with an opening to undergo Helmholtz resonance by being oscillated by one piezoelectric element disposed in the container, and calculating the speed of sound from the resonant frequency thereof.

SUMMARY OF THE INVENTION

However, the resonant frequency of a gas such as hydrogen with a low molecular weight at a high concentration is much higher than the resonant frequency of the piezoelectric element (frequency with high amplitude within frequency characteristics of piezoelectric element). Thus, with the technique disclosed in Non-Patent Document 1, the resonant frequency of the gas and the resonant frequency of the piezoelectric element greatly diverge from each other and the sound pressure by Helmholtz resonance is reduced, and thus, it is difficult to detect resonance.

In order to solve the above problem, one aspect of the present disclosure adopts the following structures. A gas sensor includes: at least one resonator; a vibrator provided on the at least one resonator; at least one converter that converts sound waves outputted from the at least one resonator to an electric signal; and a detection unit that detects a specific gas on the basis of the electric signal attained by conversion by the at least one converter, wherein the vibrator includes at least either one of: a plurality of vibrating bodies that have respectively differing frequency characteristics during vibration, that vibrate a gas inside the at least one resonator, and that output sound waves by resonance of the at least one resonator; and a heater that heats a gas inside the at least one resonator, and that outputs sound waves by resonance of the at least one resonator.

It is to be understood that both the foregoing general description and the following detailed description are exemplary and explanatory and are not restrictive of this disclosure.

BRIEF DESCRIPTION OF THE DRAWINGS

The present disclosure can be appreciated by the description which follows in conjunction with the following figures, wherein.

DETAILED DESCRIPTION OF EMBODIMENTS

Below, embodiments are explained in detail with reference to the appended figures. Embodiments are mere examples to implement the present disclosure, and shall not be interpreted to limit the technical scope of the present disclosure. In the respective figures, the same configurations are given the same reference characters. For ease of explanation, the dimensions and shapes of the illustrated parts and configurations are not necessarily true.

A gas detection device that detects hydrogen gas is described as one example of a gas sensor in the embodiments. The gas detection device may be used to detect not only hydrogen gas but other gases with a low molecular weight and a high speed of sound therein as compared to air (helium gas, for example).

Embodiment 1

Figure 1:
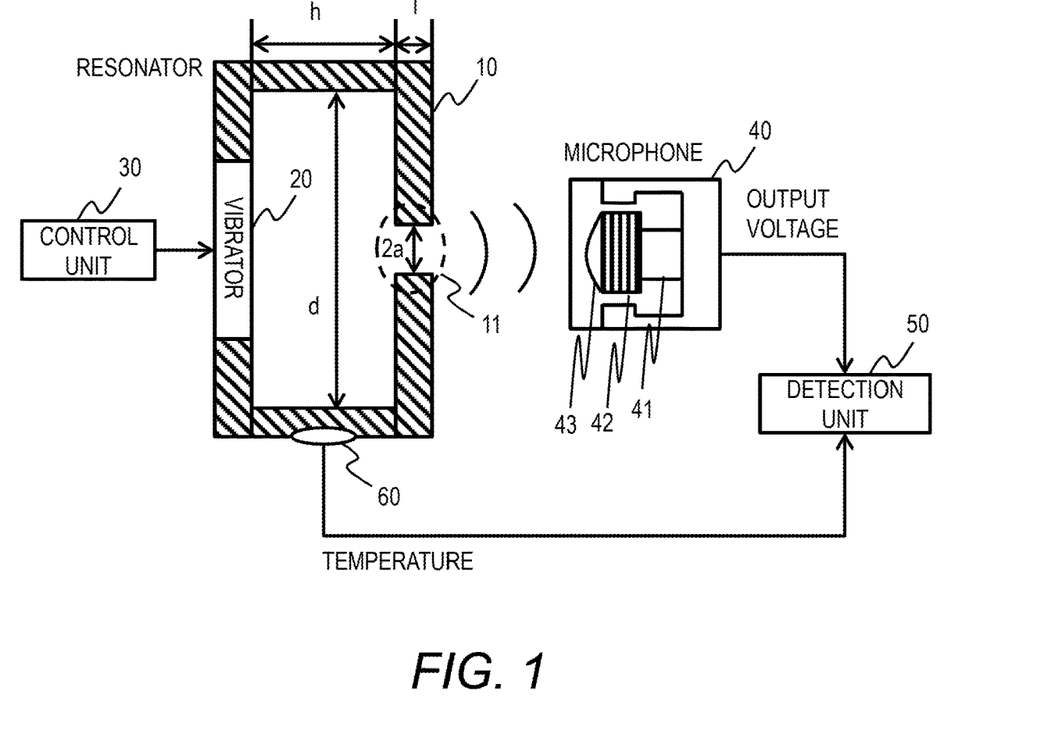
FIG. 1 is a block diagram depicting a configuration example of a gas detection device according to Embodiment 1.

FIG. 1 is a block diagram depicting a configuration example of a gas detection device. The gas detection device includes a resonator 10, a control unit 30, a microphone 40, and a detection unit 50. The resonator 10 is a container having an opening 11 (the example in FIG. 1 depicts a cross-sectional view of the resonator 10), and has attached thereto a vibrator 20 and a thermometer 60. In the example of FIG. 1, the resonator 10 is a cylinder in which the surface including the vibrator 20 is the bottom surface, and the opening 11 is circular in shape and is provided in the surface opposite to the surface including the vibrator 20. The shapes of the resonator 10 and the opening 11 as well as the location in which to provide the opening 11 are not limited to those of the example of FIG. 1.

The vibrator 20 vibrates a gas in the space inside the resonator 10. By the gas in the space inside the resonator 10 vibrating at a specific frequency (resonant frequency), a Helmholtz resonance is generated in the resonator 10. In the example of FIG. 1, the vibrator 20 is included in the resonator 10 and vibrates the gas in the resonator 10, but the vibrator 20 may be attached to the outer surface of the resonator 10, and in such a case, the vibrator 20 causes the gas inside the resonator 10 to vibrate by vibrating the resonator 10 itself. Specific examples of the vibrator 20 will be described later.

The control unit 30 controls the vibration of the vibrator 20. The control unit 30 is constituted of a processor that operates according to programs and/or a logic circuit having a specific function, for example. These components may be individual circuits, or some or all of the components may share the same circuit (including the processor). This similarly applies to detection unit 50.

The microphone 40 is a converter that converts the resonance from the resonator 10 into an electric signal. The microphone 40 is a dynamic microphone including a magnet 41, a moving coil 42, and a vibrating plate 43, for example.

The detection unit 50 is connected to the microphone 40, detects electric signals from the microphone 40, and determines the resonant frequency of the resonator 10. Also, the detection unit 50 is connected to the thermometer 60 and receives temperature information measured by the thermometer 60. The thermometer 60 is attached to the resonator 10 and measures the temperature of the gas atmosphere, for example.

Also, the detection unit 50 uses the resonant frequency and the temperature received from the thermometer 60 to calculate the hydrogen gas concentration. Specifically, the detection unit 50 uses the following formulae to calculate the hydrogen gas concentration, for example.

$$f(\omega)[Hz] = \frac{C}{2\pi}\sqrt{\frac{\pi a^2}{V(l+1.3a)}} = \frac{C}{2\pi}\sqrt{\frac{4a^2}{d^2h(l+1.3a)}} \quad \text{(Formula 1)}$$

$$C = \sqrt{\frac{\gamma RT}{M}} \quad \text{(Formula 2)}$$

In Formula 1, "f(ω)" is the resonant frequency of the resonator 10, "C" is the speed of sound, "V" is the internal volume of the resonator 10, "l" is the height of the opening 11 (thickness of the surface of the resonator 10 having the opening 11), "a" is the radius of the opening 11, "d" is the diameter of the bottom surface of the space inside the resonator 10, and "h" is the height of the space inside the resonator 10. In Formula 2, "C" is the speed of sound, "γ" is the specific heat ratio, R is the gas constant (8.31446 m$^2$ kg/s$^2$Kmol), "T" is the temperature, and "M" is the molar mass (kg/mol).

The detection unit 50 calculates the speed of sound according to the received resonant frequency using Formula 1. Next, the detection unit 50 calculates the molar mass and specific heat ratio of the gas using Formula 2 according to the calculated speed of sound and the received temperature.

The detection unit 50 may be connected to an output device (not depicted; examples include a display device or a speaker device), and output the calculated gas concentration to the output device, for example. The detection unit 50 may alternatively not output the gas concentration itself to the output device but instead output an alert to the output device if the gas concentration is within a prescribed range (such as the explosive limit, for example).

The microphone 40 may be a condenser microphone. Condenser microphones have an insulating support body, a fixed electrode, and a vibrating plate (movable electrode), for example. If the resonant frequency in air (hydrogen gas concentration of 0%) is 1000 Hz, for example, then the resonant frequency in air with a hydrogen gas concentration of 1% is 1005 Hz. In this case, the resonant frequency changes by approximately 5 Hz in relation to the 1% change in hydrogen gas concentration. On the other hand, if the resonant frequency in air (hydrogen gas concentration of 0%) is 5000 Hz, then the resonant frequency in air with a hydrogen gas concentration of 1% is 5024 Hz. In this case, the resonant frequency changes by approximately 24 Hz in relation to the 1% change in hydrogen gas concentration.

Thus, by adopting a design in which the resonant frequency of the resonator 10 is high, the sensitivity of the gas detection device to changes in hydrogen concentration is increased. Condenser microphones can detect sound waves in the high frequency range with greater ease than dynamic microphones, and thus, if the microphone 40 is a condenser microphone, sensitivity to changes in hydrogen concentration is increased.

Figure 2:
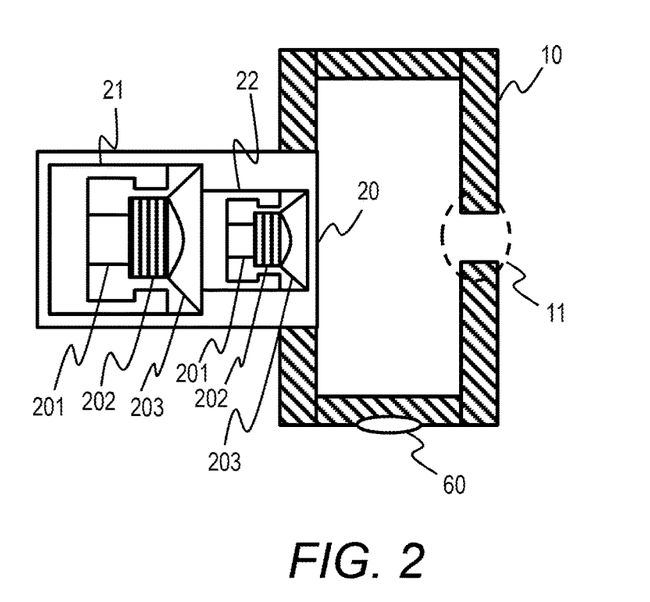
FIG. 2 is a block diagram depicting an example of a resonator according to Embodiment 1.

FIG. 2 is a block diagram depicting an example of the resonator 10. In the example of FIG. 2, the vibrator 20 is a dynamic speaker including a low frequency sound source 21 and a high frequency sound source 22, which are both vibrating bodies. The low frequency sound source 21 has frequency characteristics in which the amplitude is high (at or above a prescribed value, for example) in the low frequency range (the resonant frequency (specifically in the vicinity of 5 kHz, for example) for a case in which the hydrogen gas concentration at a prescribed temperature (293K, for example) is at the lower limit for measurement (0%, for example)). The high frequency sound source 22 has frequency characteristics in which the amplitude is high (at or above a prescribed value, for example) in the high frequency range (the resonant frequency (specifically in the vicinity of 15 kHz, for example) for a case in which the hydrogen gas concentration at a prescribed temperature (293K, for example) is at the upper limit for measurement (100%, for example)). Also, the amplitude peak in the frequency characteristics of the low frequency sound source 21, for example, is present on the low frequency side as compared to the amplitude peak in the frequency characteristics of the high frequency sound source 22. The low frequency sound source 21 and the high frequency sound source 22 are both speakers including a magnet 201, a moving coil 202, and a vibrating plate 203, for example.

The control unit 30 includes an alternating current power source, for example, and by applying an alternating current voltage with a sweeping frequency to the vibrator 20, sound is outputted from the resonator 10. The vibrator 20 includes two sound sources with differing frequency characteristics, and therefore can output sound in a wide frequency range. Specifically, the vibrator 20 can generate resonance with a high sound pressure even if the resonant frequency of the resonator 10 shifts to the high frequency side as a result of increased hydrogen gas concentration. Thus, the gas detection device can detect hydrogen gas at a wide range of concentrations. In the example of FIG. 2, the vibrator 20 includes two sound sources, but there is no limit to the number of sound sources.

In applying an alternating current voltage with a sweeping frequency to the vibrator 20, the control unit 30 may apply a differing voltage for each frequency. Specifically, the control unit 30 applies a high voltage (2Vpp, for example) at a frequency where the total sound pressure amplitude in the frequency characteristics of the low frequency sound source 21 and the high frequency sound source 22 (that is, the sound pressure amplitude in the frequency characteristics of the vibrator 20 as a whole) is less than a prescribed value, and applies a low voltage (0.15Vpp, for example) at a frequency where the total sound pressure amplitude in the frequency characteristics of the low frequency sound source 21 and the high frequency sound source 22 (that is, the sound pressure amplitude in the frequency characteristics of the vibrator 20 as a whole) is greater than a prescribed value.

As a result, the frequency characteristics of the vibrator 20 as a whole become flat (in other words, the sound pressure amplitude is not small for either the low frequency region or the high frequency region), and thus, the gas detection device can easily detect hydrogen gas at a wide range of concentrations.

Figure 3:
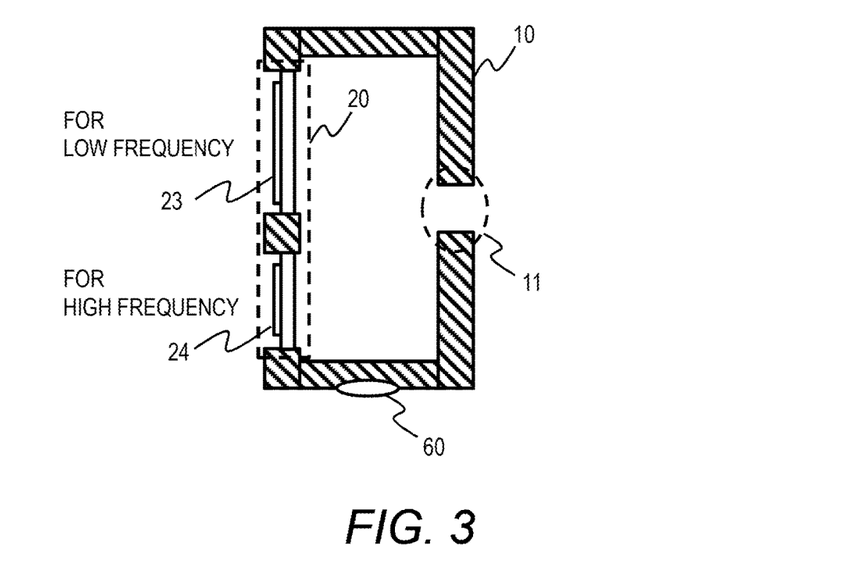
FIG. 3 is a block diagram depicting an example of a resonator according to Embodiment 1.

FIG. 3 is a block diagram depicting an example of the resonator 10. In the example of FIG. 3, the vibrator 20 includes a low frequency piezoelectric element 23 and a high frequency piezoelectric element 24, which are both vibrating bodies. The low frequency piezoelectric element 23 has frequency characteristics where the amplitude in the low frequency region is high. The high frequency piezoelectric element 24 has frequency characteristics where the amplitude in the high frequency region is high. Also, the amplitude peak in the frequency characteristics of the low frequency piezoelectric element 23, for example, is present on the low frequency side as compared to the amplitude peak in the frequency characteristics of the high frequency piezoelectric element 24.

The control unit 30 applies an alternating current voltage with a sweeping frequency to the low frequency piezoelectric element 23 and the high frequency piezoelectric element 24 included in the vibrator 20, thereby outputting a wide frequency range from the vibrator 20.

The frequency characteristics of the piezoelectric element can be designed on the basis of the parameters disclosed in the non-patent document (L. de Luca, M. Girfoglio, M. Chiatto, G. Coppola "Scaling properties of resonant cavities driven by piezo-electric actuators" Sensors and Actuators A: Physical Volume 247, 15 Aug. 2016, P. 465-474, Elsevier B.V.), for example.

Figure 4:
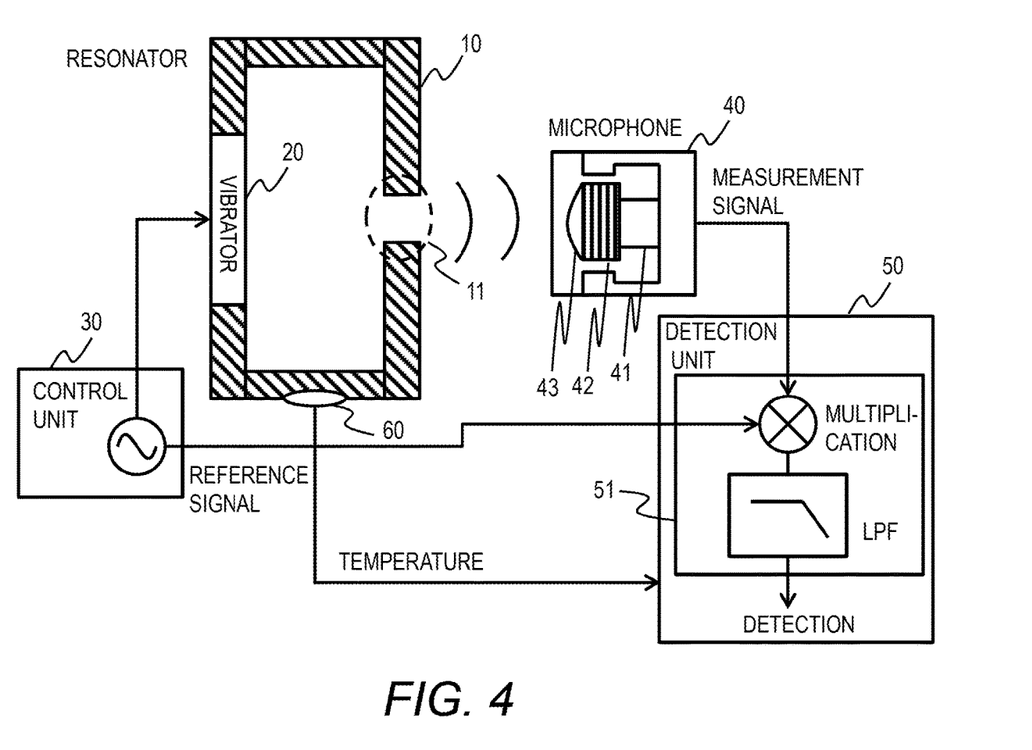
FIG. 4 is a block diagram depicting a configuration example of a gas detection device according to Embodiment 1.

FIG. 4 is a block diagram depicting a configuration example of a gas detection device. FIG. 4 depicts the detection unit 50 in detail. In the example of FIG. 4, the control unit 30 includes an alternating current power source and the detection unit 50 includes a lock-in amplifier 51. The control unit 30 applies an alternating current voltage with a sweeping frequency to the vibrator 20. Also, the control unit 30 transmits the alternating current voltage to the lock-in amplifier 51 as a reference signal.

By the lock-in amplifier 51 multiplying the reference signal by a measurement signal from the microphone, only the frequency component equal to the reference signal, among the frequency components of the measurement signal, becomes a direct current, and can pass through an LPF (low pass filter) of the lock-in amplifier 51. As a result, the detection unit 50 can detect the frequency of the measurement signal and the phase information, and furthermore reduce noise.

Figure 5:
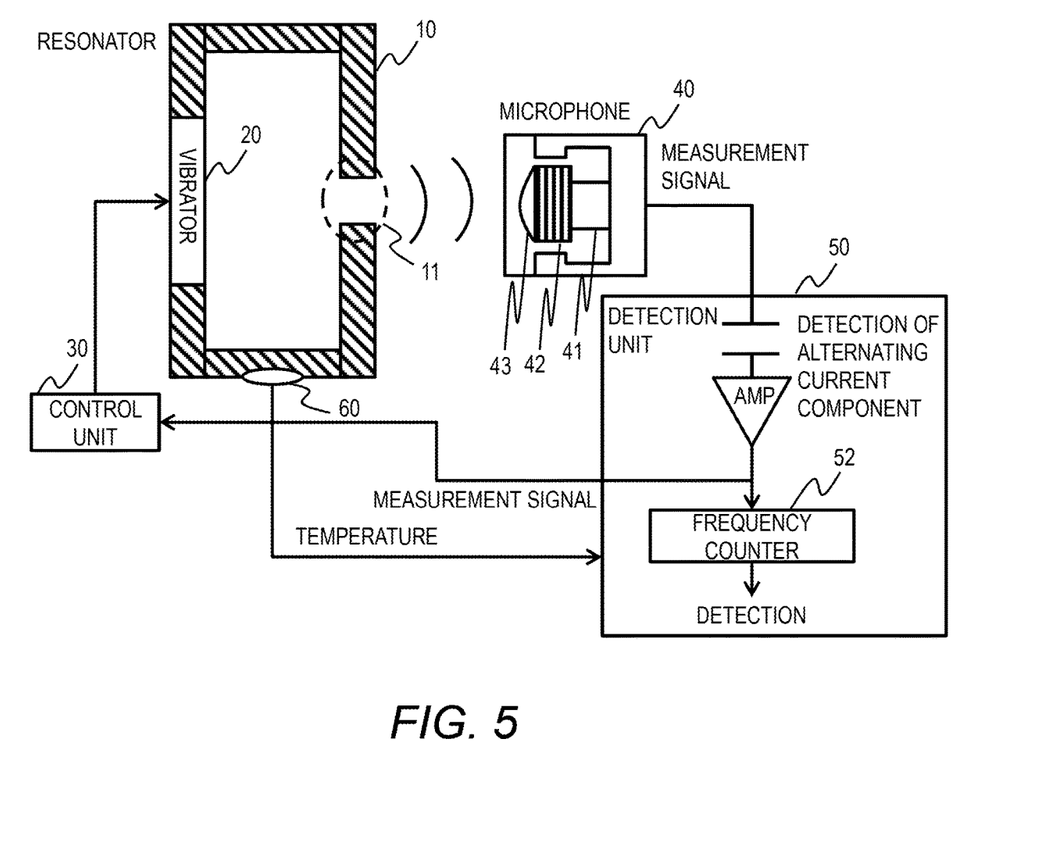
FIG. 5 is a block diagram depicting a configuration example of a gas detection device according to Embodiment 1.

FIG. 5 is a block diagram depicting a configuration example of a gas detection device. FIG. 5 depicts the detection unit 50 in detail. The control unit 30 includes an oscillation circuit, for example. In a hypothetical example, the vibrator 20 vibrates at a specific frequency due to some factor, and a Helmholtz resonance is generated in the resonator 10. In this case, the detection unit 50 receives a measurement signal attained by measurement by the microphone 40, and an alternating current component is detected from the received measurement signal and amplified by an amplifier. The amplified measurement signal is transmitted to the control unit 30 and a frequency counter 52 in the detection unit 50.

The frequency counter 52 detects the frequency of the amplified measurement signal and phase information. By the control unit 30 causing the vibrator 20 to vibrate due to oscillation by the amplified measurement signal, the Helmholtz resonance in the resonator 10 continues. In the example of FIG. 5, the control unit 30 does not need to apply a voltage with a sweeping frequency to the vibrator 20, and thus, it is possible to shorten the measurement time for the gas concentration.

Embodiment 2

Figure 6:
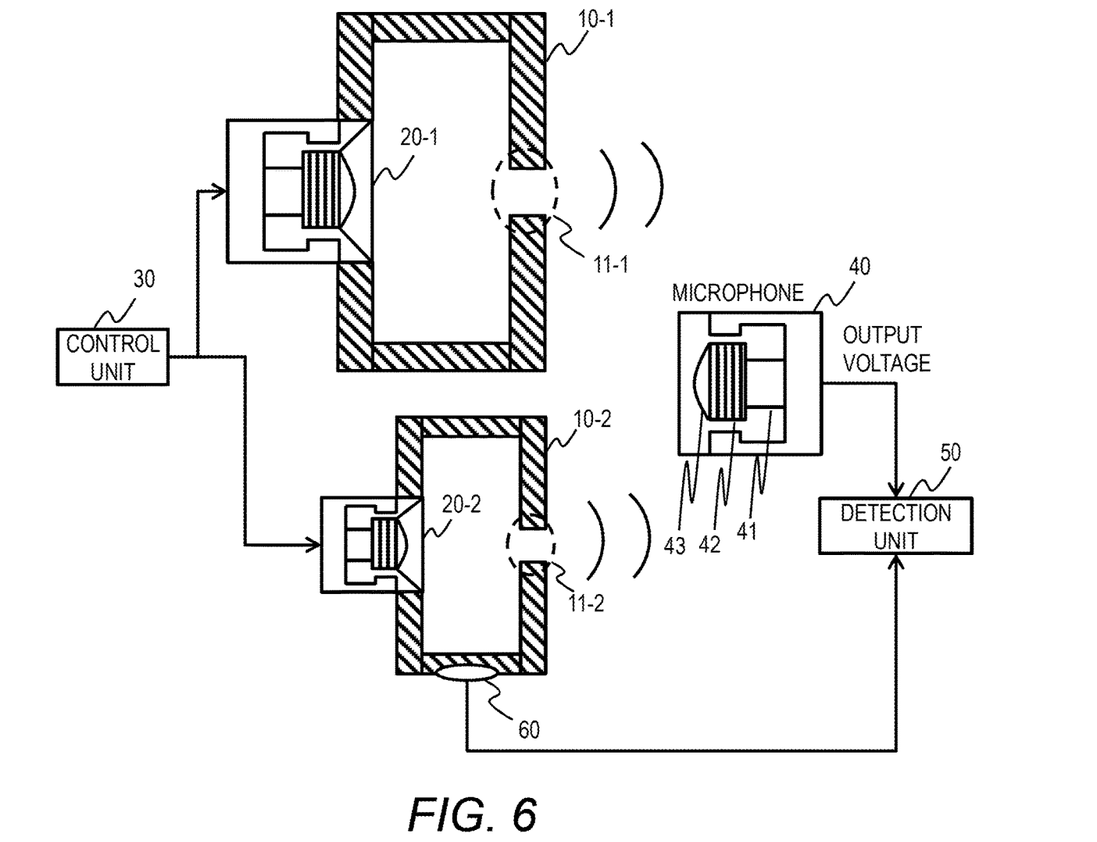
FIG. 6 is a block diagram depicting a configuration example of a gas detection device according to Embodiment 2.

Differences from Embodiment 1 will be described, and explanations of content in common with Embodiment 1 will be omitted. The gas detection device of the present embodiment includes a plurality of resonators 10. FIG. 6 is a block diagram depicting a configuration example of a gas detection device. The gas detection device includes resonators 10-1 and 10-2. The resonator 10-1 is provided with an opening 11-1 and has attached thereto a vibrator 20-1. The resonator 10-2 is provided with an opening 11-2 and has attached thereto a vibrator 20-2. In the example of FIG. 6, the thermometer 60 is attached to the resonator 10-2, but may alternatively be attached to the resonator 10-1, or be attached to both of the resonators 10-1 and 10-2.

The resonator 10-1 is designed so as to have a lower resonant frequency than the resonator 10-2 under the same conditions. The vibrator 20-1 is a speaker that has frequency characteristics where the sound pressure amplitude in the low frequency region is high, for example. The vibrator 20-2 is a speaker that has frequency characteristics where the sound pressure amplitude in the high frequency region is high, for example.

As mentioned previously, the gas detection device has a high sensitivity to changes in hydrogen gas concentration, the higher the resonant frequency to which the resonator 10 is set, and therefore can easily measure low concentrations of hydrogen gas. On the other hand, if the resonator 10 is set to a high resonant frequency, then if the hydrogen gas concentration is high, the resonant frequency is further increased, and therefore, it becomes difficult to measure high concentrations of hydrogen gas.

The gas detection device of FIG. 6 can easily measure high concentrations of hydrogen gas by the resonator 10-1 with a low resonant frequency set thereto, and can have an increased sensitivity to changes in hydrogen gas concentrations even in the low concentration range using the resonator 10-2 with a high resonant frequency setting, thereby enabling easy measurement of low concentrations of hydrogen gas.

In the example of FIG. 6, the gas detection device includes two resonators, but may include three resonators having differing resonant frequencies and frequency characteristics of the vibrator.

Figure 7:
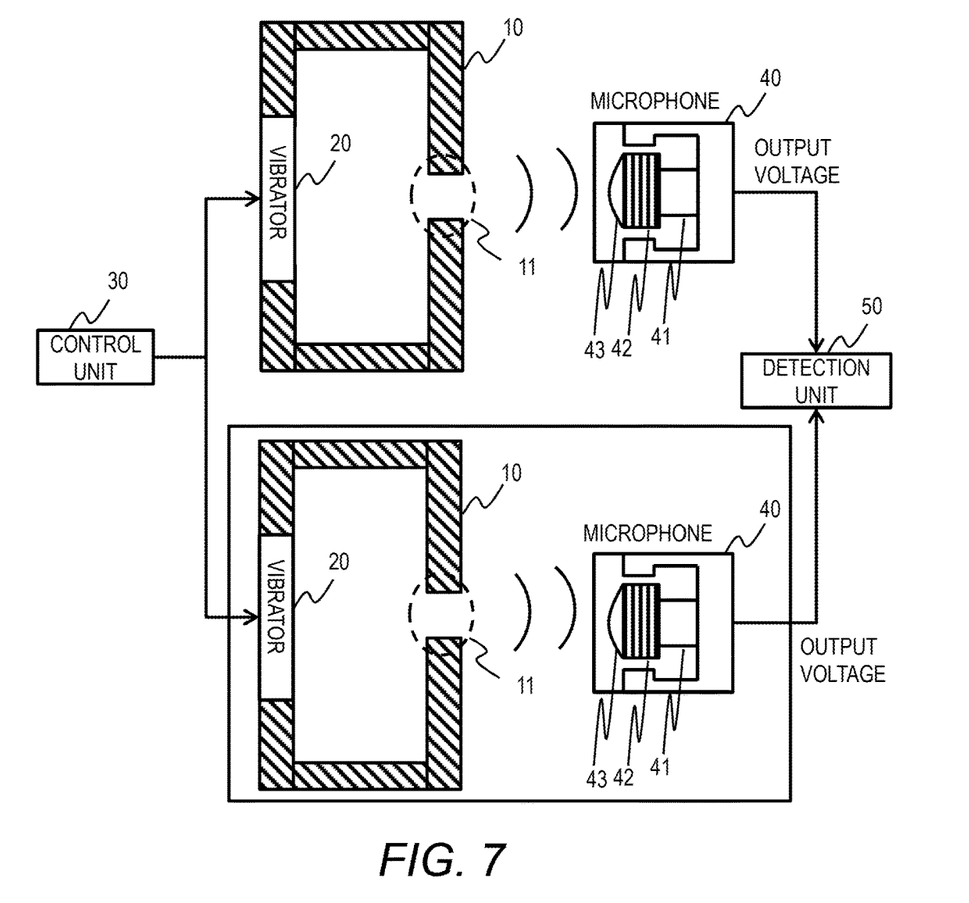
FIG. 7 is a block diagram depicting a configuration example of a gas detection device according to Embodiment 2.

FIG. 7 is a block diagram depicting a configuration example of a gas detection device. The gas detection device of FIG. 7 includes two of the same resonator 10 and two of the same microphone 40. The thermometer 60 is not attached to either of the two resonators 10. One resonator 10 and one microphone 40 are disposed in a space in which the hydrogen gas concentration is to be measured.

The other resonator 10 and other microphone 40 are disposed in a space that is filled with a specific gas composition and that has the same temperature as the space in which the hydrogen gas concentration is to be measured. Specifically, the other resonator 10 and other microphone 40 are disposed in a sealed space filled with nitrogen.

The positional relationship (including orientation) of the one resonator 10 and the one microphone 40 is the same as the positional relationship of the other resonator 10 and the other microphone 40.

The control unit 30 applies an alternating current voltage with a sweeping frequency to the two vibrators 20, for example, thereby outputting sound from the two resonators 10. The detection unit 50 does not acquire temperature information, and thus, by performing temperature correction using an output voltage from the other microphone 40 as a reference signal, the hydrogen gas concentration is calculated from the output voltage from the one microphone 40. As a result, the gas detection device of FIG. 7 can calculate the hydrogen gas concentration without using the temperature information. The vibrator 20 may include both a plurality of vibrating bodies such as the speakers and piezoelectric elements of Embodiment 1, and a heater of the following embodiment 3.

Embodiment 3

Figure 8:
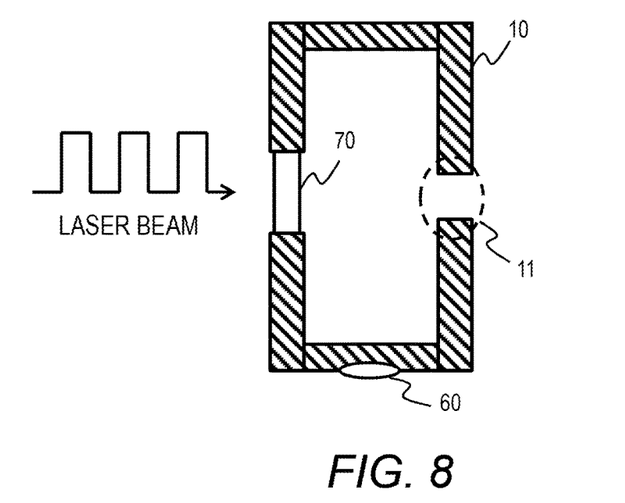
FIG. 8 is a block diagram depicting an example of a resonator according to Embodiment 3.

Differences from Embodiment 1 will be described, and explanations of content in common with Embodiment 1 will be omitted. The resonator 10 of the present embodiment uses a heater instead of a vibrator 20. FIG. 8 is a block diagram depicting an example of the resonator 10. The resonator 10 has attached thereto a heater 70.

By the heater 70 self-heating and thereby generating a sound wave having a resonant frequency, a Helmholtz resonance is generated in the resonator 10. In the example of FIG. 8, the heater 70 is made of a material that absorbs laser beams. Glass and resin films coated by a metal foil and a light absorber or the like are examples of a material that absorbs laser beams.

The control unit 30 includes a laser beam source, for example, and emits a modulated laser beam to the heater 70. By the portion of the heater 70 irradiated by the laser beam being heated, the heater generates a sound wave by the photoacoustic effect, and generates a Helmholtz resonance at a resonant frequency in the resonator 10.

Figure 9:
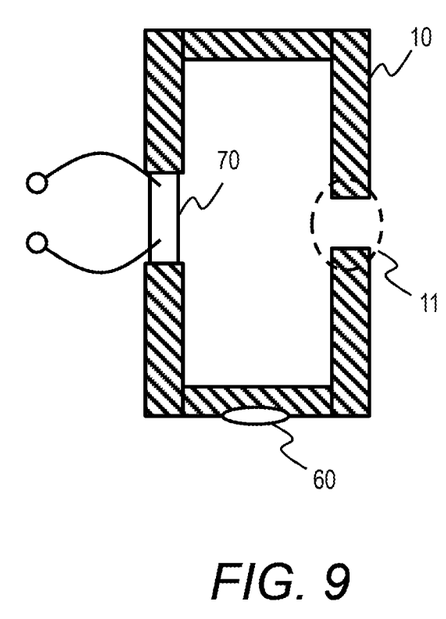
FIG. 9 is a block diagram depicting an example of the resonator according to Embodiment 3.

FIG. 9 is a block diagram depicting an example of the resonator 10. In the example of FIG. 9, the heater 70 is made of an electrically conductive material. Carbon nanotubes (CNTs) formed on glass, Ag nanowires, and the like are examples of electrically conductive materials.

The control unit 30 includes an alternating current power source, for example, and by applying an alternating current voltage to the heater 70, the heater 70 is heated. By the heater 70 being heated, the heater generates a sound wave by the thermoacoustic effect, and generates a Helmholtz resonance at a resonant frequency in the resonator 10.

In the present embodiment, sound waves generated by the heater 70 are not sound waves generated by vibrating a sound source, and therefore, do not have frequency characteristics derived from natural vibration, and have flat frequency characteristics. Thus, the gas detection device of the present embodiment can detect hydrogen gas with a high degree of sensitivity and at a wide range of hydrogen concentrations.

Embodiments are explained above, but the present disclosure is not limited to those embodiments. Each element of the embodiments described above may be easily modified, added or changed without departing from the scope of the present disclosure by a person skilled in the art. It is possible to replace a part of the configuration of one embodiment with the configuration of another embodiment, or it is possible to add a configuration of one embodiment to a configuration of another embodiment.

What is claimed is:

1. A gas sensor, comprising:
   at least one resonator;
   a vibrator provided on the at least one resonator;
   at least one converter that converts sound waves outputted from the at least one resonator to an electric signal; and
   a detection unit that detects a specific gas on the basis of the electric signal attained by conversion by the at least one converter,
   wherein the vibrator includes at least either one of:
   a plurality of vibrating bodies that have respectively differing frequency characteristics during vibration, that vibrate a gas inside the at least one resonator, and that output sound waves by resonance of the at least one resonator; and
   a heater that heats a gas inside the at least one resonator, and that outputs sound waves by resonance of the at least one resonator.

2. The gas sensor according to claim 1,
   wherein the vibrator includes the plurality of vibrating bodies,
   wherein the plurality of vibrating bodies include a first vibrating body and a second vibrating body,
   wherein, in the frequency characteristics of the first vibrating body, an amplitude at a resonant frequency of the at least one resonator is at a prescribed value or greater for when a concentration of the specific gas is at a first value, and
   wherein, in the frequency characteristics of the second vibrating body, an amplitude at a resonant frequency of the at least one resonator is at a prescribed value or greater for when a concentration of the specific gas is at a second value that is greater than the first value.

3. The gas sensor according to claim 2,
   wherein the first vibrating body is a first sound source, and the second vibrating body is a second sound source that has frequency characteristics in which an amplitude peak is present at a frequency higher than in the first sound source.

4. The gas sensor according to claim 2,
   wherein the first vibrating body is a first piezoelectric element, and the second vibrating body is a second piezoelectric element that has frequency characteristics in which an amplitude peak is present at a frequency higher than in the first piezoelectric element.

5. The gas sensor according to claim 1, further comprising:
   a control unit that controls vibration of the gas inside the at least one resonator,
   wherein the vibrator includes the plurality of vibrating bodies,
   wherein the detection unit includes a lock-in amplifier,
   wherein the control unit
   applies an alternating current voltage with a sweeping frequency to the vibrator, and
   transmits the alternating current voltage to the lock-in amplifier as a reference signal, and
   wherein the lock-in amplifier
   detects the specific gas on the basis of the electric signal attained by conversion by the at least one converter, and the reference signal.

6. The gas sensor according to claim 1, further comprising:
a control unit that controls vibration of the gas inside the at least one resonator,
wherein the vibrator includes the plurality of vibrating bodies,
wherein the detection unit
amplifies the electric signal attained by conversion by the at least one converter, and
transmits the amplified electric signal to the control unit, and
wherein the control unit controls vibration of the vibrator using the amplified electric signal received from the detection unit.

7. The gas sensor according to claim 1, further comprising:
a control unit that controls vibration of the gas inside the at least one resonator,
wherein the vibrator includes the plurality of vibrating bodies,
wherein the control unit applies an alternating current voltage with a sweeping frequency to the vibrator, and
wherein a second voltage applied at a second frequency is less than a first voltage applied at a first frequency, the first frequency being a frequency in which an amplitude in the frequency characteristics of the vibrator is at a first value, and the second frequency being a frequency in which the amplitude in the frequency characteristics of the vibrator is at a second value that is greater than the first value.

8. The gas sensor according to claim 1,
wherein the at least one resonator includes a first resonator and a second resonator,
wherein the vibrator includes the plurality of vibrating bodies,
wherein the plurality of vibrating bodies include a first vibrating body and a second vibrating body,
wherein the first resonator includes the first vibrating body,
wherein the second resonator includes the second vibrating body,
wherein under same conditions, a resonant frequency of the first resonator is lower than a resonant frequency of the second resonator,
wherein, in the frequency characteristics of the first vibrating body, an amplitude at a resonant frequency of the first resonator is at a prescribed value or greater for when a concentration of the specific gas is at a first value, and
wherein, in the frequency characteristics of the second vibrating body, an amplitude at a resonant frequency of the second resonator is at a prescribed value or greater for when a concentration of the specific gas is at a second value that is greater than the first value.

9. The gas sensor according to claim 1,
wherein the at least one resonator includes a first resonator and a second resonator,
wherein the at least one converter includes a first converter and a second converter,
wherein the first resonator and the first converter are disposed in a space where the specific gas is to be detected,
wherein the second resonator and the second converter are disposed in a space under a prescribed condition of a same temperature as the space in which the specific gas is to be detected, and
wherein the detection unit detects the specific gas on the basis of a first electric signal attained by the first converter converting a sound wave outputted by the first resonator, and a second electric signal attained by the second converter converting a sound wave outputted by the second resonator.

10. The gas sensor according to claim 1, further comprising:
a control unit that controls vibration of the gas inside the at least one resonator,
wherein the vibrator includes the heater,
wherein the heater contains a material that absorbs laser beams, and
wherein the control unit emits a laser beam to the heater.

11. The gas sensor according to claim 1, further comprising:
a control unit that controls vibration of the gas inside the at least one resonator,
wherein the vibrator includes the heater,
wherein the heater contains an electrically conductive material, and
wherein the control unit applies a voltage to the heater.

12. A gas detection method, comprising:
converting sound waves outputted from at least one resonator having a vibrator to an electric signal; and
detecting a specific gas on the basis of the electric signal attained by conversion,
wherein the vibrator includes at least either one of:
a plurality of vibrating bodies that have respectively differing frequency characteristics during vibration, that vibrate a gas inside the at least one resonator, and that output sound waves by resonance of the at least one resonator; and
a heater that heats a gas inside the at least one resonator, and that outputs sound waves by resonance of the at least one resonator.

* * * * *